United States Patent [19]

Jacobs

[11] Patent Number: 5,084,052
[45] Date of Patent: Jan. 28, 1992

[54] SURGICAL CUTTING INSTRUMENT WITH PLURALITY OF OPENINGS

[75] Inventor: Randall W. Jacobs, Santa Ana, Calif.

[73] Assignee: Baxter International Inc., Deerfield, Ill.

[21] Appl. No.: 309,268

[22] Filed: Feb. 9, 1989

[51] Int. Cl.$^5$ .............................................. A61B 17/32
[52] U.S. Cl. ..................................... 606/79; 606/170
[58] Field of Search ................. 606/170, 171, 180, 79, 606/159, 168, 83, 110; 30/29.5, 43.6, 205, 206, 223, 240, 279.2; 604/22; 128/751, 755

[56] References Cited

U.S. PATENT DOCUMENTS

| | | |
|---|---|---|
| 930,477 | 8/1909 | Hudson . |
| 1,043,408 | 11/1912 | De Vilbiss . |
| 1,923,177 | 8/1933 | Tucker . |
| 2,026,630 | 1/1936 | Harris .............................. 30/29.5 X |
| 2,243,441 | 5/1941 | Russell ............................ 30/43.6 X |
| 2,387,756 | 10/1945 | Henningsen ........................ 30/29.5 |
| 2,525,669 | 12/1947 | Hainault . |
| 2,532,370 | 12/1950 | Perrill . |
| 2,640,379 | 6/1953 | Graves . |
| 2,677,885 | 5/1954 | Chaun ............................. 30/43.6 X |
| 2,786,373 | 3/1957 | Patton . |
| 2,842,131 | 5/1957 | Smith . |
| 2,878,809 | 3/1959 | Treace . |
| 3,308,828 | 3/1967 | Pippin . |
| 3,381,373 | 5/1968 | Brown ............................. 30/29.5 |
| 3,633,583 | 1/1972 | Fishbein . |
| 4,014,342 | 3/1977 | Staub et al. . |
| 4,167,944 | 9/1979 | Banko . |
| 4,274,414 | 6/1981 | Johnson et al. . |
| 4,440,532 | 4/1984 | D'Apuzzo . |
| 4,456,010 | 6/1984 | Reimels et al. . |
| 4,466,429 | 8/1984 | Losher et al. . |
| 4,473,070 | 9/1984 | Matthews et al. . |
| 4,649,919 | 3/1987 | Thimsen et al. . |
| 4,811,734 | 3/1989 | McGurk-Burleson et al. ..... 30/29.5 X |

FOREIGN PATENT DOCUMENTS

| | | |
|---|---|---|
| 3131496A1 | 2/1983 | Fed. Rep. of Germany . |
| 783644 | 7/1935 | France . |
| 1451856 | 9/1966 | France ............................... 30/29.5 |

Primary Examiner—Michael H. Thaler
Attorney, Agent, or Firm—June M. Bostich; Frank J. Uxa

[57] ABSTRACT

A surgical cutting instrument comprising:
an outer tube sized for insertion through an opening in a patient, the outer tube having a peripheral wall, an end wall and a longitudinal axis;
a plurality of spaced apart openings in the end wall, one of the openings being larger than the other of the openings and extending proximally into the peripheral wall, each of the openings having at least one cutting edge; and
a cutting member moveable within the outer tube and having a cutting edge cooperable with the cutting edges of the openings for cutting material from within the patient.

42 Claims, 2 Drawing Sheets

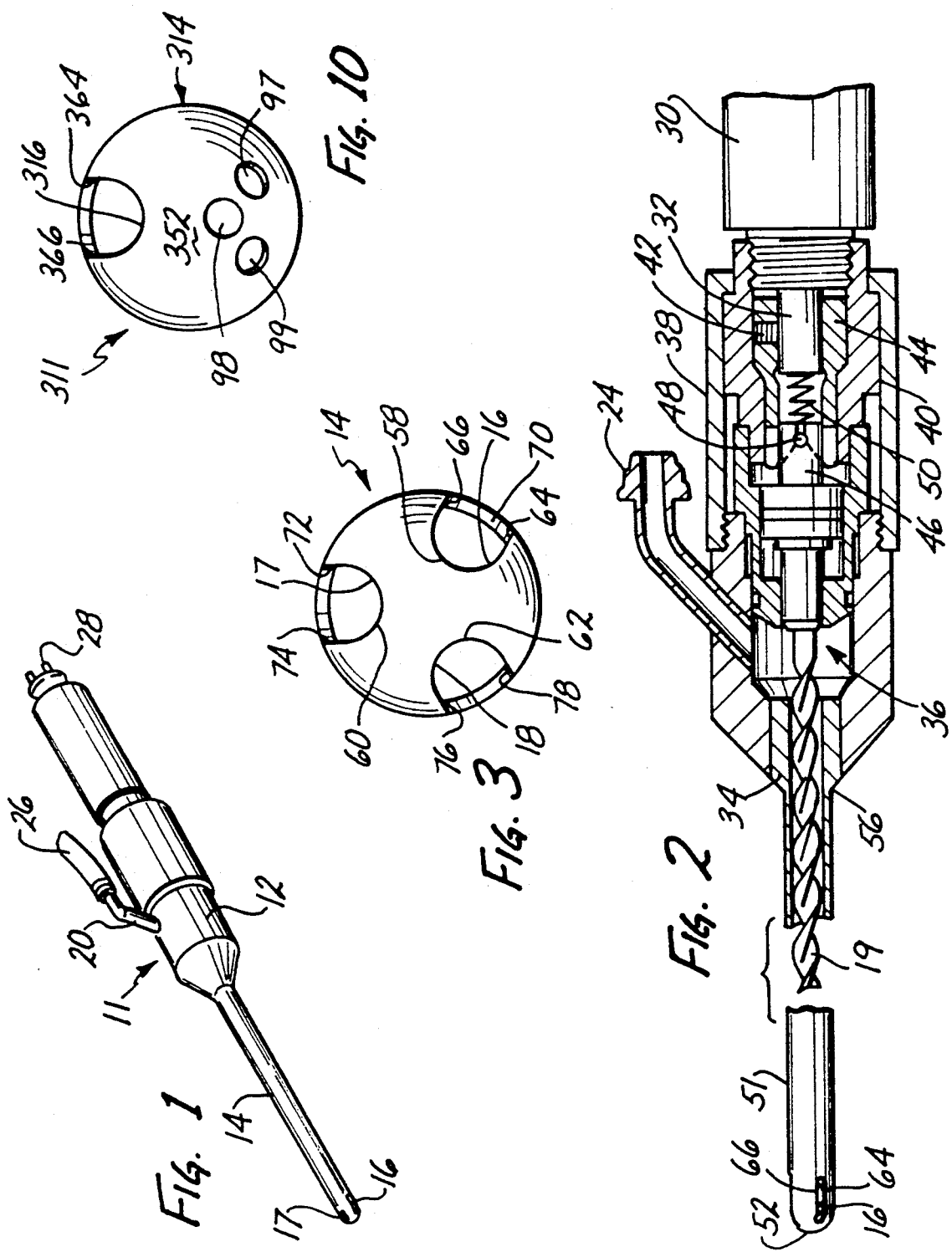

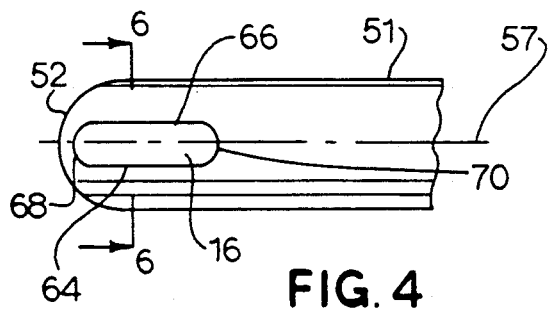
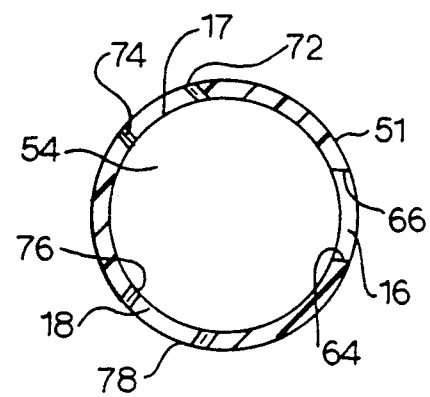
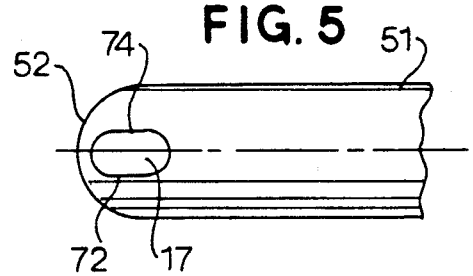
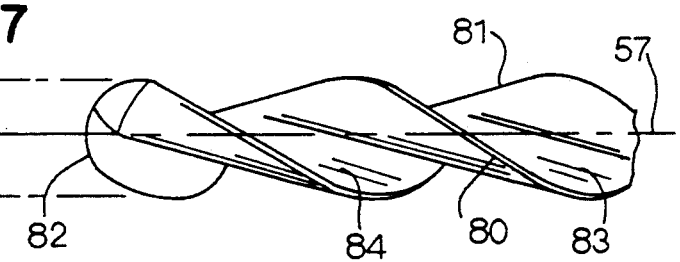
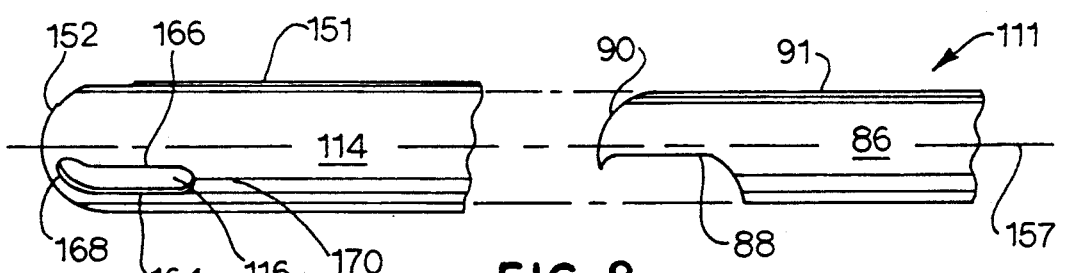
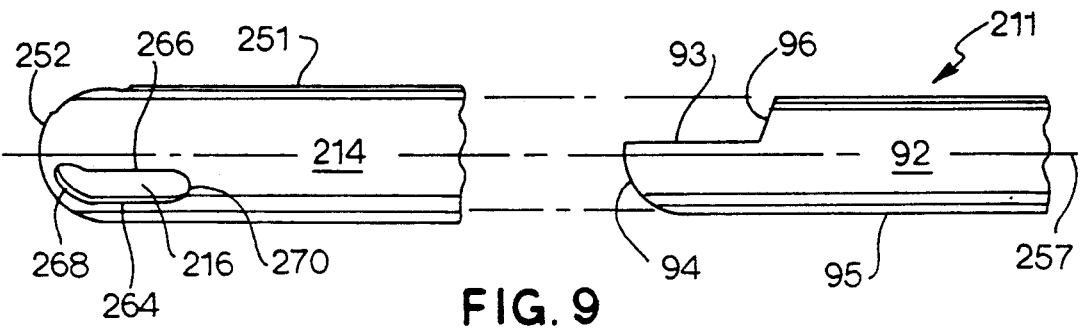

SURGICAL CUTTING INSTRUMENT WITH PLURALITY OF OPENINGS

BACKGROUND OF THE INVENTION

This invention relates to a surgical cutting instrument of the type employing rotary cutters. Instruments of this type are usable for various surgical procedures in various regions of the body, such as in the eye and knee. For example, such surgical cutting instruments may be inserted through a small opening into the knee joint and used for cutting the meniscus or other soft or hard material or tissue.

Generally, a surgical cutting instrument of this type includes an outer tube having a peripheral wall, an end wall, at least one opening in one or both of the peripheral wall and the end wall and a cutting edge defining at least a portion of the periphery of the opening. An inner cutting member, which may also be in the form of a tube, rotates or translates within the outer tube. The inner cutting member has a cutting edge that cooperates with the cutting edge or edges of the outer tube for cutting material with a shearing action as the inner cutting member is moved relative to the outer tube. One surgical cutting instrument of this general type is shown and described in Johnson et al U.S. Pat. No. 4,274,414.

Another cutting instrument of this type is the whisker cutter. In this instrument, the outer tube has a plurality of small circular openings to adapt the instrument for cutting fine hair-like projections, such as synovial tissue, from within the knee. The whisker cutter is also useful in a trimming or finishing step after the bulk of the tissue has been cut by a more aggressive cutter. Thus, for example, the main cutting is done with an aggressive cutting instrument which is then removed from the patient. The whisker cutter is then inserted into the same opening in the patient to perform the trimming or finishing. The use of two or more separate cutters is not only time consuming, but also can cause substantial additional trauma to the patient in general and to the surgical site in particular. While the whisker construction is satisfactory for certain applications, it is not suitable for a broader range of applications. For example, the round edges of the circular small holes of the outer tube do not provide as good a scissors or shearing action as is desirable for some applications.

One type of inner cutter which has been suggested is a helical or auger cutter. For example, Banko U.S. Pat. No. 4,167,944 uses a helical cutter at the distal end of a device having a outer tube with a single circular opening. Staub, et al U.S. Pat. No. 4,014,342 uses an elongated helical cutter in conjunction with an outer tube having a single opening in the distal end thereof. Thimsen, et al U.S. Pat. No. 4,649,919 uses a helical cutter in combination with an outer sheath which is open at its distal end and proximally therefrom to form diametrically opposed tabs with inwardly extending lips. Pippin, U.S. Pat. No. 3, 308,828 and Perrill U.S. Pat. No. 2,532,370 use helical cutters in conjunction with outer protective shields which do not have cutting edges or surfaces. These devices tend to become clogged with material removed from the patient's body and/or, because of the geometry of certain of these devices, are somewhat difficult to insert in the patient's body. Also, many of these devices provide end cutting or side cutting, but not both.

Notwithstanding a proliferation of known configurations for the outer tube and the inner cutting member, there are problems with poor cutting ability and inconsistent quality. In addition, cutting instruments are often classified as either aggressive cutters or non-aggressive cutters, and are not useful for both aggressive cutting and trimming or finishing, both of which may be necessary in a single surgical procedure.

SUMMARY OF THE INVENTION

This invention provides a novel surgical cutting instrument having various different features which tend to solve the problems identified above. With this invention, the surgical cutting instrument is adapted for multiple applications. Both aggressive cutting and trimming or finishing can be accomplished with a single cutting instrument. In addition, cutting ability and quality are improved, and the likelihood of clogging is reduced.

According to one feature of the invention, the outer tube has a peripheral wall, an end wall, a longitudinal axis, and a plurality of spaced apart openings in the end wall. One of the openings is larger, e.g., longer, than the other opening or openings and extends proximally into the peripheral wall which provides multiple opportunities for cutting of material. Thus, both end cutting and side cutting are possible with a single opening. In other words, the present cutting instrument is able to cut material from in front of the instrument as well as material which is located on the side relative to the instrument. This larger opening is preferably sufficiently large so that aggressive cutting is achieved using this opening. With the relatively large opening located at least partially in the peripheral wall of the outer tube, this surgical cutting instrument can also serve like a curette in cutting and scraping tissue as the outer tube of the instrument is moved generally axially. The relatively small, e.g. short, opening or openings in the outer tube provide for less aggressive cutting and are useful for trimming or finishing after the main or primary cutting has occurred. Thus, the present cutting instrument is preferably sufficiently flexible to provide both aggressive cutting and trimming or finishing, when needed. The surgeon need not withdraw and insert separate instruments to obtain each of these types of cutting. In effect, the present invention provides the advantages of both an aggressive cutter and a whisker cutter in a single cutting instrument.

In one embodiment, the present surgical cutting instrument includes an outer tube sized for insertion through an opening in a patient, a plurality of openings in the outer tube, and a cutting member rotatable within the outer tube. The outer tube has a peripheral or side wall, an end wall and a longitudinal axis. One of the openings is larger than the other opening or openings. The longer opening is in the end wall and extends proximally into the peripheral wall of the outer tube. This opening preferably has first and second proximally extending edges, at least one of which is preferably a cutting edge. The other opening or openings, preferably in the end wall, each have at least one cutting edge. The cutting member includes a cutting edge which is cooperable with the cutting edges of the openings for cutting material from within the patient. Preferably, none of the openings in the outer tube extend through, i.e. dissect, the longitudinal axis of the outer tube. Thus, the area of the end wall of the outer tube immediately surrounding the longitudinal axis preferably remains intact. This area is available for use as a bearing surface for the rotatable cutting member, if needed.

The other opening or openings (other than the larger opening) in the outer tube are preferably located in the end wall of the outer tube. In this embodiment, such other opening or openings may or may not extend proximally into the peripheral wall of the outer tube, depending, for example, on the type and degree of cutting action desired. The present cutting instrument may be constructed so that one or more of the other openings extend proximally into the peripheral wall of the outer tube, while one or more of the openings do not so extend.

The number of openings in the outer tube is preferably at least three. Particularly useful embodiments involve three openings. In one embodiment, each of the openings includes a distal end in the end wall of the outer tube. These distal ends are preferably substantially equidistantly spaced apart relative to the longitudinal axis of the outer tube.

In one embodiment, the larger of the openings preferably has first and second proximally extending edges. More preferably, the first and second proximally extending edges are spaced apart by a maximum distance in the range of about 20% to about 50% of the maximum cross-sectional distance defined by the end wall perpendicular to the longitudinal axis. For example, if the end wall is hemispherical in configuration, the maximum distance between the first and second proximally extending edges is more preferably in the range of about 20% to about 50% of the outside diameter of the end wall. Such configuration provides for effective cutting without destroying the ease of inserting a cutting instrument having a generally hemispherical end wall.

The first and second proximally extending edges are preferably mutually substantially parallel. More preferably these proximally extending edges are substantially parallel to the longitudinal axis of the outer tube. Such configuration provides for effective cutting and is relatively easy to manufacture.

The other opening or openings can have substantially the same general configuration as the larger opening except that the area defined by the other opening or openings is smaller. Thus, for example, such other opening or openings each may have first and second proximally extending edges configured similarly to the first and second proximally extending edges of the larger opening. In one embodiment all of the proximally extending edges of all of the openings are mutually substantially parallel, preferably substantially parallel to the longitudinal axis of the outer tube.

In another embodiment, each of the other openings is substantially circular in configuration. These substantially circular openings are similar to the openings employed in a whisker cutter, referred to above.

The other opening or openings may be present in the end wall, the peripheral wall or in both the end wall and peripheral wall of the outer tube. Preferably, the other opening or openings are located at least in the end wall of the outer tube.

The larger opening (in terms of open area at the outer surface of the outer tube) is preferably less than about 5 times, more preferably less than about 3 times, as large as the next largest opening. Such relationship has been found to provide for both effective aggressive cutting and effective trimming and finishing cutting, while at the same time reducing cut material clogging problems in the instrument. A particularly useful arrangement is the larger opening being about 2 times as large as the next largest opening. The other openings are preferably all substantially the same size.

Any suitable type of cutting member may be utilized in the present instrument provided that it has at least one cutting edge which functions as outlined herein. This cutting member may be a tube, like the outer tube of the cutting instrument. In one particularly useful embodiment, the inner cutting member comprises a helical cutter blade.

The helical cutter blade, preferably such a blade which functions at least in part as an auger to aid in removing cut material from the cutting site, is rotatable within the outer tube and has at least one cutting edge, preferably a plurality of, e.g., two, cutting edges, which cooperate with the cutting edges of the openings in the outer tube for cutting material from within the patient as the helical cutter blade rotates. The helical cutter blade is preferably sized to fit in and in close relation to the outer tube. This promotes the auger-like functioning of the helical cutter blade. Preferably, the helical cutter blade extends through a substantial portion of the length, more preferably through substantially the entire length, of the outer tube. The helical cutter blade includes at least one flute, and preferably a plurality of, e.g., two, flutes. These flutes or channels, which preferably run substantially the entire length of the helical cutter blade, act to aid in moving the cut material proximally of the cutting site. The helical cutter blade is preferably configured so that the lead angle of the helix is in the range of about 10 degrees to about 90 degrees, more preferably about 20 degrees to about 60 degrees and still more preferably about 30 degrees to about 45 degrees. The "lead angle" of the helix is defined as the angle of inclination of the helix from a plane that is perpendicular to the longitudinal axis of the helical cutter blade. Not only is the helical cutter blade effective, in combination with the cutting edges associated with the outer tube, to cut material from the patient, but such blade is also very effective in removing such cut material from the cutting site without clogging the instrument. This is an important feature because, for example, it allows the instrument to be operated on a continuous basis while keeping the cutting edges free of cut material.

The inner cutting member is preferably capable of being rotated relative to the outer tube, more preferably at a rate of at least about 50 rpm; and still more preferably at a rate in the range of about 1000 rpm to about 5000 rpm.

The invention, together with additional features and advantages thereof, may best be understood by reference to the following description taken in connection with the accompanying illustrative drawings.

BRIEF DESCRIPTION OF THE DRAWINGS

FIG. 1 is an isometric view of a surgical cutting instrument constructed in accordance with the teachings of this invention.

FIG. 2 is an enlarged fragmentary sectional view illustrating the coupling of the outer tube and the helical cutter blade to the handle.

FIG. 3 is a front plan view of the distal end of the outer tube shown in FIG. 1.

FIG. 4 is a fragmentary side plan view of the distal region of the outer tube shown in FIG. 1, rotated 30 degrees counterclockwise relative to FIG. 1.

FIG. 5 is a fragmentary plan view of the distal region of the outer tube shown in FIG. 1 rotated 120 degrees relative to FIG. 4.

FIG. 6 is an enlarged sectional view taken generally along line 6—6 of FIG. 4.

FIG. 7 is a fragmentary exploded side plan view of the distal regions of the helical cutter blade and outer tube shown in FIG. 1.

FIG. 8 is a fragmentary exploded side plan view of the distal regions of another outer tube/inner cutting member combination in accordance with the present invention.

FIG. 9 is a fragmentary exploded side plan view of the distal regions of an alternative outer tube/inner cutting member combination in accordance with the present invention.

FIG. 10 is a front plan view of the distal end of an additional outer tube in accordance with the present invention.

DETAILED DESCRIPTION OF THE DRAWINGS

A surgical cutting instrument, shown generally at 11, includes a suction housing member 12, a cylindrical outer tube 14 which has a first opening 16, a second opening 17, a third opening 18, and a helical cutter blade 19. A vacuum conduit 20 is secured to suction housing member 12. Vacuum conduit 20 is provided with a series of hose barb seal members 24 in order to receive and retain a vacuum pump (not shown). A hose receptor 28 is provided for a motor assembly 30 at one end and a motor shaft 32 extends to the left as shown in FIG. 2.

Outer tube 14 is provided with a sealing head plug 34 inserted into one open end of suction housing member 12. Helical cutter blade 19 is received and supported by a cutter housing member, indicated generally at 36. Helical cutter blade 18 is inserted into outer tube 14 and resides in close spaced relation thereto.

A quick disconnect nut member 38 is carried or trapped on a cutter drive coupling nut member 40. Suction housing member 12 and/or nut member 38 and/or motor assembly 30 may be utilized as a handle by a surgeon to hold cutting instrument 11 during use. A screw 42 secures a cutter drive coupling member 44 to the shaft 32 of the motor assembly 30. Cutter drive coupling member 44 is slotted at 46 and provided with a widely tapering end so as to self-seat the pin drive member 48 of helical cutter blade 19. A spring 50 is retained within cutter drive coupling member 44 and engages the proximal end of helical cutter blade 19 so as to urge helical cutter blade 19 constantly toward its distal end. For further details of the coupling of outer tube 14 and helical cutter blade 18 to suction housing member 12 and motor assembly 30 see Thimsen, et al U.S. Pat. No. 4,649,919 which is incorporated in its entirety herein by reference.

The helical cutter blade 19 is receivable and rotatable within the outer tube 14. Helical cutter blade 19 extends through substantially the entire length of outer tube 14 and is drivable, rotatable, by motor assembly 30. Vacuum or suction pressure may be applied to the helical cutter blade 19 via vacuum conduit 20 in a conventional manner. The bearing support for the rotation of the helical cutter blade 19 can be provided in whole or in part by the outer tube 14 or in any other suitable manner known in the art.

The outer tube 14 is sized for insertion through an opening, such as a puncture or incision, in a patient. For example, the outer tube 14 may be sized for insertion through an opening in the knee and may be used, for example, for cutting synovial tissue in the knee.

The outer tube 14 has a peripheral wall 51 and a curved end wall 52 at the distal end of the outer tube. Although various configurations are possible, the peripheral wall 51 is preferably cylindrical, and the end wall 52 is preferably generally hemispherical and of the same radius as the peripheral wall. The outer tube 14 has a passage 54 (FIG. 6) which extends completely through the outer tube 14 from a proximal end 56 (FIG. 2) all the way to the end of the outer tube. The passage 54 is cylindrical throughout the full length of the peripheral wall 51 and is generally hemispherical within the generally hemispherical end wall 52.

Each of the openings 16, 17 and 18 in outer tube 14 lies in both the end wall 52 and peripheral wall 51. None of these openings dissect the longitudinal axis 57 of outer tube 14. Openings 16, 17 and 18 have distal ends 58, 60 and 62, respectively, in end wall 52 which are equidistantly spaced relative to longitudinal axis 57. Thus, the angle formed by two lines drawn between any two of the distal ends 58, 60 and 62 and respectively, in end wall 52 which are equidistantly spaced relative to the longitudinal axis 57 is 120 degrees.

The first opening 16 has parallel proximally extending edges 64 and 66 which define substantial portions of the periphery of the opening. Each of the edges 64 and 66 extends proximally through end wall 52 into peripheral wall 51. At least one of the edges 64 and 66 of opening 16, and preferably both of such edges, is substantially straight as viewed in a particular direction parallel to the longitudinal axis 57 of the outer tube 14. This particular direction is looking directly along longitudinal axis 57.

The edges 64 and 66 of the first opening 16 are joined by relatively short curved end edges 68 and 70. Alternately, edges 64 and 66 may be joined by relatively short, substantially straight end edges, which embodiment is included within the scope of the present invention. Such a substantially straight end edge is particularly applicable to join the proximal ends of edges 64 and 66.

Second and third openings 17 and 18 have the same general configuration as does the first opening 16 except that the length of the proximally extending edges 72 and 74 of second opening 17 and proximally extending edges 76 and 78 of third opening 18 are shorter than proximally extending edges 64 and 66 of first opening 16. First opening 16 is about twice as large as either second opening 17 or third opening 18. All of the proximally extending edges 64, 66, 72, 74, 76 and 78 are mutually substantially parallel and are substantially parallel to the longitudinal axis 57.

Each of the edges of openings 16, 17 and 18 may be straight or beveled, as desired. The distance between parallel proximally extending edges of each of the openings 16, 17 and 18 is equal to about one third of the outside diameter of hemispherical end wall 52.

Although the helical cutter blade 19 can be of various different constructions, in this embodiment it includes mutually opposing cutting edges 80 and 81 and a generally rounded distal end 82. The cutting edges 80 and 81 can be of any configuration that will appropriately cooperate with the cutting edges of the openings 16, 17 and 18, to cut material. As shown, the cutting edges 80 and 81 extend substantially the entire length of helical cutter blade 19. However, these cutting edges may be extended only so far as needed to effectively cooperate with the cutting edges of openings 16, 17 and 18. Thus, the edges of helical cutting blade 19 proximally of this effective cutting region need not be cutting edges. Helical cutter blade 19 includes two flutes or channels 83 and 84 which run substantially the entire length of helical cutter blade 19. Helical cutter blade 19 has a lead angle of 40 degrees.

In use, the cutting instrument 11 is inserted through an opening in the knee to a region, such as the synovial tissue, which is to be cut, and the motor assembly 32 is energized to begin unidirectional rotation of the helical cutter blade 19 within the outer tube 14. This moves the cutting edges 80 and 81 along the cutting edge 66 of the first opening 16 and the cutting edges 74 and 78 of the openings 17 and 18 to provide cutting along such cutting edges. Because first opening 16 extends proximally into peripheral wall 51 a longer distance than does either of openings 17 and 18 and because first opening 16 is larger than either of openings 17 and 18, more aggressive cutting of the tissue occurs at first opening 16 than at openings 17 and 18. Thus, if the surgeon wishes to obtain aggressive cutting, he/she would orient cutting instrument 11 so that first opening 16 is located in relative proximity to the tissue to be cut. On the other hand, if less aggressive cutting is desired, the surgeon would orient cutting instrument 11 so that one or both of openings 17 and 18 are located in relative proximity to the tissue to be cut.

Cutting instrument 11 is particularly applicable when both aggressive and non-aggressive cutting are needed in a single surgical procedure. For example, the major amount of the cutting can be accomplished with the first opening 16 in relative proximity to the tissue to be cut. After this major cutting, cutting instrument 11 is reoriented, without being withdrawn from the patient, so that the openings 17 and 18 are in relative proximity to the tissue to be cut. With cutting instrument 11 so reoriented, trimming and/or other finishing of the remaining tissue is accomplished using the relatively non-aggressive cutting obtained at the openings 17 and 18. This feature of being able to accomplish both aggressive and non-aggressive cutting without changing cutting instruments and without having to withdraw the instrument from the patient is an important advantage of the present invention.

Because first opening 16 extends proximally from the end wall 52 to the peripheral end wall 51 to some extent, first opening 16 can be used to cut material in front and to the side of instrument 11 at the same time. Openings 17 and 18 also extend proximally from the end wall 52 into the peripheral wall 51 of outer tube 14. Thus, openings 17 and 18 can be used to cut material in front and to the side of instrument 11 at the same time.

The auger-like action of the helical cutter blade 19 aids in transporting the cut material proximally from the cutting site, thus reducing clogging of the instrument by the cut material. Suction is applied through the passage 20 so as to remove the cut or severed material after it is cut so that the cutting instrument 11 need not be withdrawn from the incision to accomplish this.

FIG. 8 illustrates another embodiment which is structured and functions in a manner similar to the embodiment illustrated in FIGS. 1 to 7 except as expressly set forth below. Components of the embodiment of FIG. 8 which correspond to components of the embodiment of FIGS. 1 to 7 are identified by the same reference numeral increased by 100.

Referring now to FIG. 8, outer tube 114 is structured identically to outer tube 14.

Inner tube 86 is sized and adapted to rotate within outer tube 114 and includes a curved cutting edge 88 which cooperates with the cutting edges of first opening 116 and openings 117 and 118 to cut material from the patient. Inner tube 86 is hollow, has a curved distal end wall 90 and a cylindrical peripheral wall 91 and is associated with suction housing member 12 and motor assembly 30 in a manner analogous to how helical cutter blade 19 is associated with these components. Thus, as inner tube 86 rotates in outer tube 114, suction is drawn through the hollow space defined by inner tube 86. This suction urges cut material proximally from the cutting site. As with cutting instrument 11, cutting instrument 111 allows for both aggressive and non-aggressive cutting of tissue without withdrawing the instrument from the patient.

FIG. 9 illustrates another embodiment which is structured and functions in a manner similar to the embodiment illustrated in FIGS. 1 to 7 except as expressly set forth below. Components of the embodiment of FIG. 9 which correspond to components of the embodiment of FIGS. 1 to 7 are identified by the same reference numerical increased by 200.

Referring now to FIG. 9, outer tube 214 is structured identically to outer tube 14.

Inner tube 92 is sized and adapted to rotate within outer tube 214 and includes a curved cutting edge 93 extending from a generally hemispherical distal end 94 into a cylindrical peripheral wall 95. This cutting edge 93 is joined with a slanting cutting edge 96 in peripheral wall 95. Inner tube 92 is hollow and is associated with the suction housing member and motor assembly in a manner analogous to how helical cutter blade 19 is associated with these components. The cutting edges 93 and 96 cooperate with the cutting edges of first opening 216 and openings 217 and 218 in outer tube 214 to cut material from the patient. As inner tube 92 rotates in outer tube 214, suction is drawn through the hollow space defined by inner tube 92. This suction urges cut material proximally from the cutting site. As with cutting instrument 11, cutting instrument 211 allows for both aggressive and non-aggressive cutting of tissue without withdrawing the instrument from the patient.

FIG. 10 illustrates a still further embodiment which is structured and functions in a manner similar to the embodiment illustrated in FIGS. 1 to 7 except as expressly set forth below. Components of the embodiment of FIG. 10 which correspond to components of the embodiment of FIGS. 1 to 7 are identified by the same reference number increased by 300.

A helical cutter blade structured identically to helical cutter blade 19 is provided and rotatable within outer tube 314.

Outer tube 314 includes a first opening 316. A series of three small circular openings 97, 98 and 99 are provided in the distal end 352 of outer tube 314. Circular openings 97, 98 and 99 include cutting edges 100, 101 and 102, respectively, and are located generally opposite from first opening 316 in distal end 352, as shown in FIG. 10. In this embodiment, the small circular openings are located only in the distal end wall 352. However, it is within the scope of the invention that the peripheral wall of instrument 311 can also have one or more of such small circular openings, or that one or more of such smaller circular openings can be in both the end wall and the peripheral wall of outer tube 314.

The small circular openings 97, 98 and 99 may be likened to the whisker openings noted previously.

As the helical cutter blade rotates within outer tube 314, the cutting edges of this blade cooperate with the cutting edges of first opening 316 and circular openings 97, 98 and 99 to cut material from the patient. As the helical outer blade rotates in outer tube 314, suction is drawn through the hollow space defined by outer tube 314. This suction urges cut material proximally from the cutting site. As with cutting instrument 11, cutting instrument 311 allows for both aggressive and non-aggressive cutting of tissue without withdrawing the instrument from the patient. In addition, inner tubes 86 and 92 can be used in place of the helical cutter blade in cutting instrument 311, and such modification is within the scope of the present invention.

Although exemplary embodiments of the invention have been shown and described, many changes, modifications and substitutions may be made by one having ordinary skill in the art without necessarily departing from the spirit and scope of this invention.

What is claimed is:

1. A surgical cutting instrument comprising:
    an outer tube sized for insertion through an opening in a patient, said outer tube having a peripheral wall, an end wall, and a longitudinal axis;
    not more than about three spaced apart openings in said end wall, one of said openings being larger and longer in the direction of said longitudinal axis than the other of said openings and extending proximally into said peripheral wall, each of said openings having at least one cutting edge; and
    a cutting member moveable within said outer tube and having a cutting edge cooperable with said cutting edges of said openings for cutting synovial tissue from within the patient.

2. The instrument of claim 1 wherein none of said openings extends through said longitudinal axis and said cutting member is rotatable within said outer tube.

3. The instrument of claim 1 wherein said end wall is curved.

4. The instrument of claim 1 wherein said end wall is substantially hemispherical, and said peripheral wall is substantially cylindrical.

5. The instrument of claim 1 wherein each of said openings extends proximally into said peripheral wall.

6. The instrument of claim 1 wherein none of the other of said openings extend proximally into said peripheral wall.

7. The instrument of claim 1 wherein said cutting member is a tube.

8. The instrument of claim 1 wherein said cutting member is a helical cutting member.

9. The instrument of claim 1 wherein the number of said openings is at least three.

10. The instrument of claim 1 wherein the number of said openings is three.

11. The instrument of claim 1 wherein each of said openings includes a distal end in said end wall, and said distal ends are substantially equidistantly spaced apart relative to said longitudinal axis.

12. The instrument of claim 1 wherein said larger opening has first and second proximally extending edges.

13. The instrument of claim 12 wherein said first and second proximally extending edges are spaced apart by a maximum distance in the range of about 20% to about 50% of the maximum cross-section distance defined by said end wall perpendicular to said longitudinal axis.

14. The instrument of claim 12 wherein said first and second proximally extending edges are mutually substantially parallel.

15. The instrument of claim 14 wherein said first and second proximally extending edges are substantially parallel to said longitudinal axis.

16. The instrument of claim 1 wherein each of said opening have first and second proximally extending edges.

17. The instrument of claim 16 wherein said first and second proximally extending edges of each of said openings are spaced apart by a maximum distance in the range of about 20% to about 50% of the maximum cross-section distance defined by said end wall perpendicular to said longitudinal axis.

18. The instrument of claim 14 wherein said first and second proximally extending edges of each of said openings are mutually substantially parallel.

19. The instrument of claim 18 wherein said first and second proximal extending edges of each of said openings are substantially parallel to said longitudinal axis.

20. The instrument of claim 1 wherein the other of said openings each have substantially the same configuration.

21. The instrument of claim 1 wherein the other of said openings each have a substantially circular configuration.

22. The instrument of claim 1 wherein said larger opening is less than about 5 times as large as the next largest of said openings.

23. The instrument of claim 1 wherein said larger opening is less than about 3 times as large as the next largest of said openings.

24. The instrument of claim 1 wherein said larger opening is about 2 times as large as the next largest of said openings.

25. A surgical cutting instrument comprising:
    an outer tube sized for insertion through an opening in a patient, said outer tube having a substantially cylindrical peripheral wall, a substantially hemispherical end wall and a longitudinal axis;
    no more than about three spaced apart openings in said end wall, each of said openings having first and second proximally extending edges, one of said openings being larger and longer in the direction of said longitudinal axis than the other of said openings and extending proximally into said peripheral wall, each of said openings having at least one cutting edge; and
    a cutting member rotatable within said outer tube and having a cutting edge cooperable with said cutting edges of said openings for cutting synovial tissue from within the patient.

26. The instrument of claim 25 wherein none of said openings extends through said longitudinal axis.

27. The instrument of claim 25 wherein each of said openings extends proximally into said peripheral wall.

28. The instrument of claim 25 wherein each of said openings includes a distal end in said end wall, and said distal ends are substantially equidistantly spaced apart relative to said longitudinal axis.

29. The instrument of claim 25 wherein said first and second proximally extending edges of each of said openings are spaced apart by a maximum distance in the range of about 20% to about 50% of the maximum cross-section distance defined by said end wall perpendicular to said longitudinal axis.

30. The instrument of claim 25 wherein said first and second proximally extending edges of each of said openings are mutually substantially parallel.

31. The instrument of claim 25 wherein the other of said openings each have substantially the same configuration.

32. The instrument of claim 25 wherein said larger opening is less than about 5 times as large as the next largest of said openings.

33. The instrument of claim 25 wherein said larger opening is less than about 3 times as large as the next largest of said openings.

34. The instrument of claim 25 wherein said larger opening is about 2 times as large as the next largest of said openings.

35. The instrument of claim 25 wherein said first and second proximally extending edges of each of said openings are substantially parallel to said longitudinal axis.

36. A surgical cutting instrument comprising:
an outer tube sized for insertion through an opening in a patient, said outer tube having a substantially cylindrical peripheral wall, a substantially hemispherical end wall and a longitudinal axis;
not more than about three spaced apart openings in said end wall, one of said openings having first and second proximally extending edges and extending proximally into said peripheral wall, the other of said openings having a substantially circular configuration, each of said openings having at least one cutting edge; and
a cutting member rotatable within said outer tube and having a cutting edge cooperable with said cutting edges of said openings for cutting synovial tissue from within the patient.

37. The instrument of claim 36 wherein none of said openings extends through said longitudinal axis.

38. The instrument of claim 36 wherein none of the other of said openings extend proximally into said peripheral wall.

39. The instrument of claim 36 wherein the number of said openings is at least three.

40. The instrument of claim 36 wherein said first and second proximally extending edges are spaced apart by a maximum distance in the range of about 20% to about 50% of the maximum cross-section distance defined by said end wall perpendicular to said longitudinal axis.

41. The instrument of claim 36 wherein said first and second proximally extending edges are mutually substantially parallel.

42. The instrument of claim 36 wherein said first and second proximally extending edges are substantially parallel to said longitudinal axis.

* * * * *